US010500094B2

(12) United States Patent
Buzawa et al.

(10) Patent No.: US 10,500,094 B2
(45) Date of Patent: *Dec. 10, 2019

(54) CONVEX CONTACT PROBE FOR THE DELIVERY OF LASER ENERGY

(71) Applicants: IRIDEX Corporation, Mountain View, CA (US); National University Hospital (Singapore) PTE Ltd., Singapore (SG); National University of Singapore, Singapore (SG)

(72) Inventors: David Buzawa, San Jose, CA (US); Paul T. K. Chew, Singapore (CN)

(73) Assignees: IRIDEX Corporation, Mountain View, CA (US); National University Hospital (Singapore) PTE LTD, Singapore (SG); National University of Singapore, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/616,768

(22) Filed: Jun. 7, 2017

(65) Prior Publication Data
US 2018/0000638 A1      Jan. 4, 2018

Related U.S. Application Data

(63) Continuation of application No. 14/750,729, filed on Jun. 25, 2015, now Pat. No. 9,700,461.
(Continued)

(51) Int. Cl.
*A61F 9/008* (2006.01)
*A61F 9/007* (2006.01)
*A61F 9/009* (2006.01)

(52) U.S. Cl.
CPC .............. *A61F 9/008* (2013.01); *A61F 9/009* (2013.01); *A61F 9/00781* (2013.01);
(Continued)

(58) Field of Classification Search
CPC .................. A61F 9/008; A61F 9/00781; A61F 2009/00865; A61F 2009/00868; A61F 2009/00891
See application file for complete search history.

(56) References Cited

U.S. PATENT DOCUMENTS 5,151,098 A * 9/1992 Loertscher .......... A61F 9/00802
606/16
5,217,452 A * 6/1993 O'Donnell .............. A61F 9/008
128/898
(Continued)

FOREIGN PATENT DOCUMENTS

JP       H07250862 S    10/1995
JP       2002282298     10/2002

OTHER PUBLICATIONS

Gaasterland et al., "Initial Experience With a New Method of Laser Transscleral Cyclophotocoagulation for Ciliary Ablation in Severy Galucoma", Tr. Am. Ophth. Soc., vol. LXXXX, 1992, 22 pages.
(Continued)

*Primary Examiner* — Rex R Holmes
(74) *Attorney, Agent, or Firm* — Kilpatrick Townsend and Stockton LLP

(57) ABSTRACT

Systems, devices, and methods for treating a glaucomatous eye are provided. Embodiments may provide a treatment probe for treating an eye of a patient. The treatment probe may have an elongate body with a contact surface at a distal end of the elongate body. A treatment fiber or light source may be housed in the treatment probe and may be configured to direct treatment energy from the contact surface. The contact surface may be configured to couple to a surface of the eye to deliver the energy into the target area. In many embodiments the contact surface may have a convex configuration with a rounded outer shape and edge that facilitates the sweeping of the probe surface across the eye during
(Continued)

treatment delivery. In some embodiments the probe may be swept in arc motions while delivering treatment energy to the eye.

18 Claims, 13 Drawing Sheets

Related U.S. Application Data

(60) Provisional application No. 62/018,345, filed on Jun. 27, 2014.

(52) U.S. Cl.
CPC ............... *A61F 2009/00865* (2013.01); *A61F 2009/00868* (2013.01); *A61F 2009/00891* (2013.01)

(56) References Cited

U.S. PATENT DOCUMENTS

| | | | |
|---|---|---|---|
| 5,372,595 A | 12/1994 | Gaasteland et al. | |
| 5,514,125 A | 5/1996 | Lasser et al. | |
| 5,549,596 A | 8/1996 | Latina | |
| 5,549,632 A | 8/1996 | Lai | |
| 5,968,033 A * | 10/1999 | Fuller | A61B 18/203 606/9 |
| 6,059,772 A | 5/2000 | Hsia et al. | |
| 8,945,103 B2 | 2/2015 | Chew et al. | |
| 2006/0021623 A1 | 2/2006 | Miller et al. | |
| 2006/0187978 A1 | 8/2006 | Telfair et al. | |
| 2010/0076419 A1 | 3/2010 | Chew et al. | |
| 2015/0305938 A1 * | 10/2015 | Vold | A61B 90/30 606/6 |

OTHER PUBLICATIONS

Goel et al., "Aqueous Humor Dynamics: A Review" The Open Ophthalmology Journal, 2010, vol. 4, pp. 52-59.
Iridex, G-Probe™ Operator Manual 13105-EN Rev D May 2013, 17 pages.
Kosoko et al., "Long-Term Outcome of Initial Ciliary Ablation With Contact Diode Laser Transscleral Cyclophotocoagulation for Severe Glaucoma", Ophthalmology, vol. 103, No. 8, Aug. 1996, 9 pages.
Shields, edited by Thomas, MD et al., "Surgical Anatomy in Glaucoma. Glaucoma Surgery", Harvard Medical School, Massachusetts Eye and Ear Infirmary, Boston, Massachusetts, Mosby Year Book, 1992, 5 pages.
Tan et al., "Mircopulse Transscleral Diode Laser Cyclophotocoagulation in the Treatment of Refractory Glaucoma," *Clinical and Experimental Ophthalmology*, 38:266-272 (2010), 7 pages.

* cited by examiner

CONVEX CONTACT PROBE FOR THE DELIVERY OF LASER ENERGY

CROSS-REFERENCE TO RELATED APPLICATIONS

This application is a continuation of U.S. patent application Ser. No. 14/750,729 filed Jun. 25, 2015, now U.S. Pat. No. 9,700,461, which claims priority to and the benefit of U.S. Provisional Patent Application No. 62/018,345 filed on Jun. 27, 2014, the contents of which are incorporated herein by reference in their entirety for all purposes.

BACKGROUND OF THE INVENTION

Field of the Invention

The present invention is directed generally to medical devices, systems, and methods, particularly for treatment of an eye. In particular, embodiments of the present invention are directed toward contact probes for the delivery of laser energy, and more particularly to contact probes that are used for lowering the intraocular pressure (IOP) in human eyes afflicted with glaucoma.

Glaucoma is a leading cause of blindness. Glaucoma involves the loss of retinal ganglion cells in a characteristic pattern of optic neuropathy. Untreated glaucoma can lead to permanent damage of the optic nerve and resultant visual field loss, which can progress to blindness. The loss of visual field due to glaucoma often occurs gradually over a long time and may only be recognized when the loss is already quite advanced. Once lost, this damaged visual field can never be recovered.

Raised intraocular pressure (IOP) is a significant risk factor for developing glaucoma. IOP is a function of production of aqueous humor by the ciliary body of the eye and its drainage through the trabecular meshwork and all other outflow pathways including the uveoscleral pathway. Aqueous humor is a complex mixture of electrolytes, organics solutes, and other proteins that supply nutrients to the non-vascularized tissues of the anterior chamber of the eye. It flows from the ciliary bodies into the posterior chamber, bounded posteriorly by the lens and the ciliary zonule and bounded anteriorly by the iris. Aqueous humor then flows through the pupil of the iris into the anterior chamber, bounded posteriorly by the iris and anteriorly by the cornea. In the conventional aqueous humor outflow path, the trabecular meshwork drains aqueous humor from the anterior chamber via Schlemm's canal into scleral plexuses and the general blood circulation. In open angle glaucoma there is reduced flow through the trabecular meshwork. In angle closure glaucoma, the iris is pushed forward against the trabecular meshwork, preventing the egress of fluid.

Uveoscleral outflow is a non-conventional pathway that is assuming a growing importance in the management of glaucoma. In uveoscleral outflow, aqueous humor enters the ciliary muscles from the anterior chamber and exits through the supraciliary space and across the anterior or posterior sclera. Uveoscleral outflow may contribute significantly to total aqueous humor outflow.

Currently, glaucoma therapies aim to reduce IOP by either limiting the production of aqueous humor or by increasing the outflow of aqueous humor. Medications such as beta-blockers, carbonic anhydrase inhibitors, etc., are used as the primary treatment to reduce the production of aqueous humor. Medications may also be used as the primary therapy to increase the outflow of the aqueous humor. Miotic and cholinergic drugs increase the trabecular outflow, while prostaglandin drugs, for example, Latanoprost and Bimatoprost, increase the uveoscleral outflow. These drugs, however, are expensive and have undesirable side effects, which can cause compliance-dependent problems over time.

Surgery may also be used to increase the outflow or to lower the production of aqueous humor. Laser trabeculoplasty is the application of a laser beam over areas of the trabecular meshwork to increase the outflow. Cyclocryotherapy and laser cyclophotocoagulation are surgical interventions over the ciliary processes to lower the production of aqueous humor. Although they may be effective, these destructive surgical interventions are normally used as a last resource in the management of glaucoma due to the risk of the severe complication of phthisis bulbi. Other adverse side effects of cyclodestructive surgical procedures may include ocular hypotony and inflammation of the anterior eye segment, which may be associated with an increased incidence of macula complications. Still other adverse side effects include transient hyphaema and exudates in the anterior chamber, uveitis, visual loss, and necrotizing scleritis.

In laser transscleral cyclophotocoagulation, high intensity continuous wave (CW) infrared laser energy is directed through selected portions of the pars plicata region to the ciliary body, structures under the scleral layers and the overlying conjunctiva. Selected portions of the ciliary body and related processes are permanently destroyed, thereby decreasing the overall production of aqueous humor. Laser energy may be directed through air to a patient seated at a special slit lamp. Alternatively, laser energy may be delivered through the use of fiber optic handpieces placed in contact with the patient's eyeball. In both laser energy delivery methods, however, accurately and repeatedly directing a laser beam a subsurface non-visible target such as the ciliary body can be challenging for a surgeon. Thus, contact handpiece probes (for example, the G-Probe available through IRIDEX Corporation of Mountain View, Calif. and described in U.S. Pat. No. 5,372,595, the full disclosure of which is incorporated herein by reference in its entirety) have been designed to facilitate the aiming of a laser toward the pars plicata region of the ciliary body. The G-Probe, for example, has special contours that facilitate consistent placement and aiming of the probe relative to external landmark structures of the eye, thereby guiding a treatment and decreasing the likelihood of incidental laser exposure to unintended structures.

While the prior systems, methods, and devices have provided advancements in the art, further improvements are desired.

BRIEF SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

Embodiments of the present invention provide systems, devices, and methods for treating an eye, in particular examples, a glaucomatous eye. An amount of laser energy is delivered to the pars plana of the eye by a hand-holdable device. This device comprises a hand-holdable elongate member and a contact member disposed on an end of the elongate member. A contact surface of the contact member is placed in direct contact with the eye so that a reference edge of the contact member aligns with an external reference feature of the eye, usually the limbus, and a treatment axis defined by the elongate member may form a predetermined, non-zero angle with the optical axis of the eye. Typically, amounts of laser energy are applied to the eye in an annular pattern positioned significantly posterior to that typically used for cyclodestructive procedures, thus avoiding most or all photocoagulation of the ciliary bodies. The delivered laser energy dose is still sufficient to effect a reduction of intraocular pressure. This reduction may endure for long periods after treatment. Thus, this invention effects a long-term reduction in intraocular pressure while reducing or avoiding permanent destruction of aqueous producing structures in the eye and undesired thermal damage to adjacent tissue structures, both of which are typical of conventional laser cyclophotocoagulation procedures.

Accordingly, an object of the present invention is to provide an improved laser energy delivery handpiece.

Another object of the present invention is to provide a laser energy delivery handpiece with a handpiece axis that is substantially perpendicular to the eye, i.e., substantially normal to the surface of the eye.

Another object of the present invention is to provide a laser energy delivery handpiece that has a contact surface with a single radius of curvature across the contact surface.

Still another object of the present invention is to provide a laser energy delivery handpiece that has a contact surface with substantially no sharp edges.

A further object of the present invention is to provide a laser energy delivery handpiece with a contoured contact surface and a protruding hemispherical laser output tip.

Still a further object of the present invention is to provide a laser energy delivery handpiece.

A further object of the present invention is to provide a laser energy delivery handpiece that helps a surgeon to keep the direction of the laser beam precisely pointed toward the internal intraocular, invisible target.

Yet another object of the present invention is to provide a laser energy delivery handpiece that allows delivery of treatment either with a series of individual precisely-spaced applications and/or with continuously sliding arc motions.

These and other objects of the invention are achieved in a laser energy delivery handpiece characterized by an axis and adapted to receive a fiber optic for laser surgery on a patient's eye. The eye has a shaped sclera, a limbus and an optic axis. Portions define a convex contact surface that does not conform to the shape of the sclera at the limbus when the axis of the handpiece forms a predetermined angle relative to the external surface of the eye.

In another embodiment of the present invention, a laser energy delivery handpiece receives a fiber optic for laser surgery on an eye and has an input end, an output end, a top, a bottom and sides. The fiber optic has an optic axis. The eye has a shaped sclera, limbus, and an optic axis. The handpiece includes a body for holding the fiber optic and a contoured end portion. The contoured end portion has an end surface with an opening for the fiber optic. The end surface does not conform to the shape of the sclera at the limbus when the optic axis of the fiber optic is substantially perpendicular to the eye. In some embodiments, it may be preferable for the end surface to have a convex configuration. The convex configuration may be rounded with a radius of curvature.

An aspect of the invention provides a laser treatment method for an eye, the eye having a pars plana posterior to a pars plicata and a pre-laser treatment intraocular pressure. An amount of pulsed laser energy is delivered to the pars plana of the eye. The amount is insufficient to effect therapeutic photocoagulation and is sufficient to maintain a reduction from the pre-laser treatment intraocular pressure. Typically, the amount is sufficient to maintain the reduction from the pre-laser treatment intraocular pressure more than 5 months after the pulsed laser energy is delivered. The amount may be sufficient to increase uveoscleral outflow. The amount of energy will typically be delivered without direct posterior eye pain alleviating agent delivery, and without excessive pain.

Generally, a laser delivery tip of a probe is positioned in contact with an outer surface of the eye and the amount of pulsed laser energy is delivered from the positioned probe so that the pulsed laser energy is oriented toward a first pars plana region and such that permanent thermal damage to the pars plicata is avoided. The eye has an optical axis, and the probe will typically be oriented so that the pulsed laser energy is angularly offset from the optical axis when the tip of the probe is positioned in contact with the surface of the eye. The probe may define a treatment axis along which the pulsed laser energy is delivered, and the probe will typically be positioned so that the treatment axis is generally perpendicular with the surface of the eye when the tip of the probe is positioned in contact with the surface of the eye.

To position the tip of the probe in contact with the surface of the eye, a reference structure may be provided for some embodiments of a contact surface of the probe. The reference structure may be positioned in alignment with a reference feature of the eye. The laser delivery tip will be disposed along the contact surface so that the pulsed laser energy is delivered posteriorly to a limbus of the eye by over 2 mm. The first pars plana region to where the pulsed laser energy is delivered may be posterior to the limbus by 3 mm. The reference feature of the eye will typically comprise the limbus, and the reference structure of the contact surface may comprise an edge or other feature of the probe separated from the laser delivery tip by over 2 mm. Optionally, the reference structure may be a concave feature along an edge of the convex contact surface. The pulsed laser energy is delivered to the first pars plana region while the probe is held at a fixed position against the eye. The probe may be incrementally moved around the limbus so as to sequentially treat a plurality of circumferentially offset regions of the pars plana. The offset regions define angular widths about the ocular axis of from 5 to 20 degrees. The pulsed laser energy may be delivered to the first pars plana region for at least about 1 second.

The pulsed laser energy will generally comprise pulsed infrared laser energy, for example, laser energy having a wavelength of 810 nm. The total laser energy directed to the pars plana will generally be less than 75 J. In some embodiments, the pulsed laser energy may be delivered from a plurality of fixed probe locations. Each pulse will typically have an energy of less than 1 mJ, and total laser energy directed to the pars plana may be less than 40 J. The pulsed laser energy will typically have a duty cycle of about 50% or less, or even a duty cycle of about 20% or less.

In many embodiments, a first portion of the pulsed laser energy is directed to a first arc about the optical axis of the eye. The first arc will typically be disposed on a superior region of the eye. A second portion of the pulsed laser beam may be directed toward a second arc about the optical axis of the eye, the second arc being spaced away from the first arc and disposed along an inferior region of the eye.

In some cases, the tip of the probe may be positioned in contact with the surface of the eye by sliding the tip of the probe in alignment with the pars plana during delivery of the pulsed laser energy.

Another aspect of the invention provides a method of reducing excessive intraocular pressure in an eye. A pulsed laser beam is transmitted to an annular pattern of tissue regions of an eye by the following steps. A tip of a probe is positioned in contact with the surface of the eye in a position at least 3 mm posterior of the limbus. The pulsed laser beam is directed from the positioned tip of the probe from the position toward an associated tissue region of the eye such that associated tissue region is treated and the coagulation within the eye is inhibited. The tip of the probe may be re-positioned in contact with the surface of the eye in another position disposed at least 3 mm posterior of the limbus and circumferentially offset from the treated region about an optical axis of the eye and the pulsed laser beam is again directed from the probe to an associated tissue region until the circumferential series of tissue regions have been treated. The pulsed laser beam is delivered while the probe is maintained at each of the positions toward the associated tissue regions of the eye such that an aggregate amount of the pulsed laser beam delivered to the tissue regions alleviates the excessive intraocular pressure more than five months after the tissue regions have been treated.

Another aspect of the invention provides a method for treating an eye by reducing intraocular pressure. A tip of a probe is positioned in contact with the surface of the eye so that the tip of the probe is posterior the limbus of the eye by a desired distance. The tip of the probe is moved across the surface of the eye while the tip of the probe is maintained at the desired distance posterior the limbus of the eye. Pulsed laser energy is delivered toward a region of the eye posterior to the limbus while the tip of the probe is slid across the eye and maintained in contact with the surface of the eye.

Another aspect of the invention provides a hand-holdable device for delivering optical energy to treat an eye. The device comprises a hand-holdable elongate member and a contact member disposed on an end of the elongate member. The hand-holdable elongate member defines a treatment axis and is adapted to receive an optical fiber for delivering optical energy along the treatment axis. The contact member comprises a reference element and defines a contact surface. The contact surface is placed in direct contact with the eye and the reference element is aligned with a reference feature of the eye. The contact surface does not conform with a region of the surface of the eye and the treatment axis forms a predetermined, non-zero angle with the optical axis of the eye.

The contact surface can be placed in direct contact with the eye and the reference element can be aligned with a reference feature of the eye such that the treatment axis is perpendicular to the surface of the eye.

The contact surface may be convex and may not conform to the shape of the sclera of the eye at the limbus of the eye when the contact surface is placed in direct contact with the eye and the reference element is aligned with the reference feature of the eye.

The device may further comprise an optical energy source coupled to the elongate member. The delivered optical energy may comprise light energy from one or more light emitting diodes of the optical energy source. Typically, the delivered optical energy may comprise light energy from one or more lasers of the optical energy source. The delivered optical energy may be pulsed and have a duty cycle of about 50% or less or even about 20% or less.

The hand-holdable device will typically be adapted to deliver optical energy to a region of the eye posterior to the limbus when the contact surface is placed in direct contact with the eye and the reference element is aligned with a reference feature of the eye. The region of the eye posterior to the limbus may be selected from the group consisting of the pars plana of the eye, the pars plana-pars plicata junction of the eye, and the posterior portion of the pars plicata of the eye.

The contact surface of the contact member may define a protruding optical energy delivery tip disposed along the treatment axis.

Some embodiments of the contact surface may include a reference feature. The reference feature may be a concave arc along a portion of the perimeter of the contact surface shaped to conform with the limbus of the eye.

An optical energy output aperture may be spaced away from the reference edge by at least about 3 mm to facilitate optical irradiation over at least one of the pars plana of the eye, the pars plana-pars plicata junction, and the posterior portion of the pars plicata of the eye.

Another aspect of the invention provides a device for delivering optical energy to treat an eye, the eye having a pars plana. The device comprises a handpiece, a contact member, and a laser tip. A contact member is disposed on an end of the handpiece. The contact member comprises a target tissue reference element and a treatment site spacing reference element and defines a contact surface. The laser delivery tip is adapted to couple with an optical energy source. The laser delivery tip is positioned relative to the target tissue reference element such that when the contact surface is placed in direct contact with an outer surface of the eye with the target tissue reference element aligned with a reference feature of the eye and optical energy is delivered from the laser delivery tip, the optical energy is directed toward the pars plana at an associated treatment site. The laser delivery tip is positioned relative to the treatment site spacing reference element such that a circumferential series of treatment sites are defined when the contact surface is repeatedly placed in direct contact with an outer surface of the eye with the target tissue reference element aligned with a reference feature of the eye and the treatment site spacing reference element aligned with a feature of a prior treatment and delivering an amount of pulsed laser energy to the pars plana of the eye at an associated treatment site. Delivery of an amount of pulsed laser energy from the circumferential series of treatment sites to the pars plana that is insufficient to effect therapeutic photocoagulation can be sufficient to maintain a reduction from the pre-laser treatment intraocular pressure, for example, by increasing uveoscleral outflow.

In another aspect of the invention, a handpiece which is adapted to direct and deliver optical energy in a predetermined direction and is suitable for delivery of optical energy to a patient's eye is provided. The predetermined direction is defined as the optical axis of the handpiece. The eye has a shaped sclera, a cornea, a limbus, and an optical axis. The handpiece incorporates pieces, portions or features that aid in the repeatable application of the handpiece with respect to certain features of the patient's eye. These reference features may be either permanent or temporary. They are provided with respect to treatment angle or direction of the optical output axis, with the treatment axis essentially not parallel to the optical axis of the patient's eye. They may be provided with one or more of the following parameters: locational position, indentation pressure, or spacing between discrete treatment sites.

In many embodiments, the method of delivery of optical energy from its source to its treatment target includes one or more optical fibers.

In many embodiments, the source of optical energy delivered is intended to be one or more lasers.

In many embodiments, the source of optical energy delivered is intended to be one or more light emitting diodes (LEDs).

In many embodiments, the treatment angle/direction is essentially normal, i.e., perpendicular, to the reference surface. The reference surface may be, for example, the sclera or the cornea.

In many embodiments, the feature facilitating placement with respect to a reference surface is one or more curves or facets approximating a portion of a circle. The feature facilitating placement with respect to a reference surface may be one or more curves or facets approximating a portion of a circle.

In many embodiments, the locational reference is at least partly derived from the limbus, i.e., the ocular region of intersection and transition between the corneal and scleral curves.

In many embodiments, the specific dimensional reference from the limbus may be 0 to 4 mm posterior to the limbus.

In many embodiments, the reference for indentation depth or pressure is at least partly derived from the scleral surface.

In many embodiments, the indentation depth measured from the reference surface in its natural position is between 0 and 1.5 mm.

In many embodiments, the reference for indentation depth or pressure is at least partly derived from the corneal surface.

In many embodiments, the reference for spacing between adjacent treatment sites is at least partly derived from one or more previous treatment sites. The spacing between adjacent treatment sites may be such so as to permit 1 to 6 application sites per clock-hour, i.e., 5 to 30 degree angular spacing, or 12 to 72 sites per full treatment circumference.

In some embodiments, a laser treatment method for an eye is provided where the eye has a pars plana posterior to a pars plicata and a pre-laser treatment intraocular pressure. The method may include providing a treatment probe for treating the eye of the patient. The treatment probe may include an elongate body defining a handle having a proximal end and a distal end. The treatment probe may further include a contact member coupled with the distal end of the handle. The contact member may include a convex contact surface for coupling with a surface of the eye. A treatment fiber may extend along the elongate body and may be configured for delivering a treatment laser to the eye from a distal end of the treatment fiber. The method may further include placing the convex contact surface of the treatment probe on the surface of the eye of the patient and aligning the treatment probe with a treatment region of the eye that is posterior to the limbus of the eye. Thereafter, the method may include delivering the treatment laser to the treatment region of the eye.

Optionally, the method may further include sliding the convex contact surface of the probe across the surface of the eye and maintaining a desired distance posterior from the limbus of the eye while sliding the convex contact surface of the probe across the surface of the eye. The treatment laser may be delivered while sliding the convex contact surface of the probe across the surface of the eye. In some embodiments, the convex contact surface may be slid by sliding the convex contact surface in an arc motion while maintaining the alignment of the treatment probe with the treatment region of the eye. The convex contact surface may be slid in a less than 180° arc motion on a first region of the eye. Optionally, sliding the convex contact surface may comprise sliding in a 140-160° arc motion. In some embodiments, the convex contact surface may be slid by sliding between 1-10 traverses in the arc motion in less than 100 seconds (e.g., 60 seconds or so). Optionally, the convex contact surface may be slid by sliding between 5-10 traverses in the arc motion in 45-55 seconds. In some treatments, 1 traverse may exceed 100 seconds. In further embodiments 2 traverses may exceed 100 seconds. In some embodiments, the convex surface may be slid by sliding the convex contact surface in a less than 180° arc motion on a second region of the eye—the second region of the eye being opposite from the first region. In some embodiments, the treatment laser may comprise pulsed laser energy (e.g., pulsed infrared laser energy) as the convex contact surface is slid across the treatment region of the eye. The pulsed laser energy may preferably have a duty cycle between 25%-45% and a period of 1 to 5 ms when delivering the laser treatment in a sliding manner. Preferably, the duty cycle may be between 28-32% when delivering the laser treatment in a sliding manner. These ranges may also be advantageous for transscleral treatment delivery.

In many embodiments, the convex contact surface does not conform to the sclera of the eye. Optionally, the distal end of the treatment fiber may protrude from the convex contact surface. Preferably, in some embodiments, the distal end of the treatment fiber protrudes by at least 0.15 mm from the convex surface, and often does not protrude by more than 0.4 mm from the convex contact surface. Optionally, the distal end of the treatment fiber does not protrude by more than 0.25 mm from the convex contact surface. While use of a protruding fiber might be somewhat surprising for the intended use of the probe in sliding along an outer surface of the eye, a limited protrusion distance and rounded fiber shape, when combined with the adjacent convex surface, has been found (via work in connection with the present invention) to provide an advantageous combination of good energy coupling (between the probe and the target tissues) and an automatic, sliding smooth motion. A fiber with core diameter of 0.6 mm has been found to be compatible with this smooth, sliding motion when its tip is shaped approximately into a hemisphere and the fiber is positioned to protrude less than 1 mm (0.4 mm, for example) from the adjacent convex surface. In some embodiments, the treatment probe may further include a registration feature for coupling with a portion of the eye to align the distal end of the treatment fiber with the treatment region of the eye. (See FIG. 8). In some embodiments, the treatment laser may be delivered by delivering a train of laser beam pulses so as to induce a therapeutic response without coagulation—the beneficial response mitigating of pressure within the eye.

In some embodiments, a treatment probe for treating a portion of the eye is provided. The treatment probe may include an elongate body defining a handle having a proximal end and a distal end. The treatment probe may further include a contact member coupled with the distal end of the elongate body. The contact member may include a convex contact surface for coupling with a surface of the eye. A treatment fiber may extend along the elongate body and be configured for delivering a treatment laser to the eye from a distal end of the treatment fiber.

In some embodiments, the convex contact surface has a circular cross-section with a radius of less than 12 mm. Optionally the cross-sectional radius may be between 2-10 mm. In some embodiments, the convex contact surface of the contact member may have a 5-50 mm radius of curvature, or may be planar. Optionally, the distal end of the treatment fiber may protrude distally from the convex contact surface. In some embodiments, the contact member may further include a registration feature for aligning the treatment probe with a limbus of the eye.

In some embodiments, the distal end of the treatment fiber may be positioned between 2-4 mm from an edge of the registration feature. The distal end of the treatment fiber may be centered on the convex contact surface. Optionally, the distal end of the treatment fiber may be between 2-4 mm from an edge of the convex contact surface.

In further embodiments, a system of treating an eye of a patient for glaucoma is provided. The system may include a console for generating a treatment laser for treating the eye. The system may further include a treatment probe configured to operatively couple with the console to deliver the treatment laser from the console toward the eye of the patient. The treatment probe may include an elongate body defining a handle having a proximal end and a distal end. The distal end of the elongate body may include a convex contact surface for coupling with a surface of the eye. A treatment fiber may extend along the elongate body and be configured for delivering a treatment laser to the eye from a distal end of the treatment fiber.

In some embodiments, the treatment probe may further include an illumination light conduit for delivering illuminating light to the eye from a distal end of the illumination light conduit. An edge of the ciliary process of the eye may be illuminated by directing illuminating light from the distal end of the illumination light conduit of the treatment probe to the eye. The distal end of the treatment fiber of the treatment probe may be positioned per the illuminated edge of the ciliary process. Methods may further include delivering the treatment laser to the eye from the distal end of the treatment fiber while the treatment probe is positioned per the illuminated edge of the ciliary process.

In some embodiments, the edge of the ciliary process of the eye may be illuminated by delivering illumination light at an angle ranging from 30-60° from the visual axis of the eye. In some embodiments, the edge of the ciliary process of the eye may be illuminated by delivering illumination light through the cornea and parallel to the visual axis of the eye of the patient. Optionally, the illumination light may be delivered through the pupil of the eye of the patient. In some embodiments, the edge of the ciliary process of the eye may be illuminated by delivering illumination light through the cornea directly at the angle of the anterior chamber.

In some embodiments, the distal end of the illumination light conduit may be manually adjustable such that the illumination light conduit is reconfigurable to deliver light at different angles relative to the eye and/or to different regions of the eye. Thus, in some embodiments, the method may include adjusting the distal end of the illumination light conduit such that illumination light is delivered through the cornea and parallel to the visual axis of the eye while the contact surface of the probe is placed on the surface of the eye. Optionally, the distal end of the illumination light conduit may be adjusted such that illumination light is delivered through the pupil of the eye. In some embodiments, the distal end of the illumination light conduit may be adjusted such that illumination light is delivered at an angle ranging from 30-60° from the visual axis of the eye while the contact surface of the probe is placed on the surface of the eye. In some embodiments, the distal end of the illumination light conduit may be adjusted such that illumination light is delivered directly at the angle of the anterior chamber while the contact surface of the probe is placed on the surface of the eye.

In some embodiments, a treatment probe for treating an eye of a patient for glaucoma is provided. The treatment probe may include an elongate body defining a handle having a proximal end and a distal end. A treatment fiber may be housed in the elongate body and configured for delivering a treatment laser to the eye from a distal end of the treatment fiber. An illumination light conduit may be housed in the elongate body and configured for delivering illuminating light to the eye from a distal end of the illumination light conduit. The treatment probe may further include a convex contact surface for sweeping along a surface of the eye. The distal end of the illumination light conduit may be configured to deliver illumination light at an angle ranging from 30-60° from the visual axis of the eye when the contact surface of the treatment probe couples with the surface of the eye. Optionally, the distal end of the illumination light conduit may be configured to deliver illumination light through the cornea and parallel to the visual axis of the eye of the patient when the contact surface of the treatment probe couples with the surface of the eye. In some embodiments, the distal end of the illumination light conduit may be configured to deliver illumination light through the pupil of the eye when the contact surface of the treatment probe couples with the surface of the eye. In some embodiments, the distal end of the illumination light conduit may be configured to deliver illumination light through the cornea directly at the angle of the anterior chamber when the contact surface of the treatment probe couples with the surface of the eye.

In some embodiments, the distal end of the illumination light conduit may be manually adjustable such that the illumination light conduit is reconfigurable to deliver light at different angles relative to the eye and/or to different regions of the eye. Optionally, the illumination light conduit may branch off such that the illumination light conduit comprises a plurality of distal ends for delivering illumination light from a plurality of points.

In some embodiments, the distal end of the illumination light conduit may terminate at the contact surface of the treatment probe. In some embodiments, the illumination the light conduit may branch out such that the illumination light conduit comprises a first distal end and a second distal end for delivering illumination light from a plurality of points. The first distal end and the second distal end of the illumination light conduit may terminate on both sides of the distal end of the treatment fiber such that illumination light is directed in the same plane as the treatment laser.

In some embodiments, a system for treating an eye of a patient for glaucoma is provided. The system may include a console for generating a treatment laser for treating the eye and for generating an illumination light for illuminating the ciliary body of the eye. The system may further include a treatment probe configured to operatively couple with the console to deliver the treatment laser and the illumination light from the console toward the eye of the patient. The treatment probe may include an elongate body defining a handle having a proximal end and a distal end. A treatment fiber may be housed in the elongate body and configured for delivering a treatment laser to the eye from a distal end of the treatment fiber. An illumination light conduit may be housed in the elongate body and configured for delivering illuminating light to the eye from a distal end of the illumination light conduit. The treatment probe may further include a convex contact surface for sweeping along a surface of the eye.

In yet another embodiment, a treatment probe for treating an eye of a patient for glaucoma may be provided. The treatment probe may comprise an elongate body defining a handle having a proximal end and a distal end. A light source may be housed in the elongate body and have a light transmitting surface oriented for delivering a treatment beam to the eye from the distal end of the elongate body. The treatment probe may also include an illumination light source housed in the elongate body and configured for delivering illuminating light to the eye from a distal end of the body. For example, a treatment probe may house one or more laser diodes, one or more light emitting diodes, or combinations thereof for providing illumination light and treatment light to an eye.

DETAILED DESCRIPTION OF THE INVENTION

The subject matter of embodiments of the present invention is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Figure 1A:
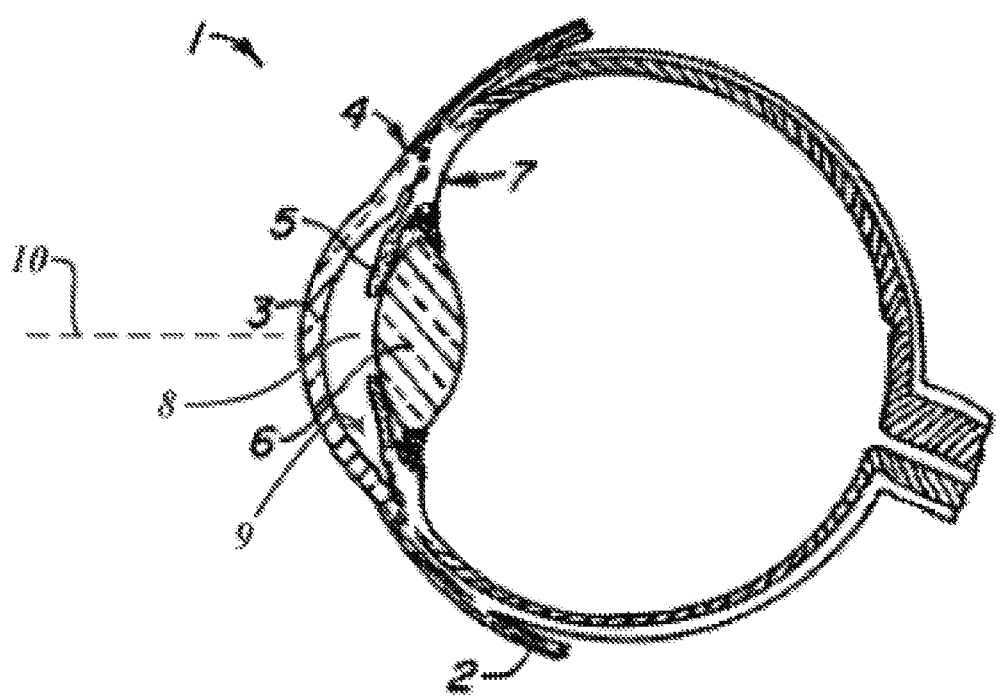
FIG. 1A shows the anatomy of an eye with relevant parts labeled to provide anatomical references.

FIG. 1A shows the anatomy of an eye 1 with relevant parts labeled to provide anatomical references. The sclera 2 is a tough sheath around the eye which meets the cornea 3 at a circular junction called the limbus 4. Behind the cornea 3 lies the iris 5, the lens 6 and the ciliary body and related processes 7. The anterior chamber is the fluid-filled compartment within the eye 1 just in front of the pupil 8. Viewed in profile, the anterior chamber is bounded by the domed cornea 3 in front and by the colored iris 5 behind. Where the cornea 3 and the iris 5 converge they form an angle 9 referred to herein as the angle of the anterior chamber. Further eye 1 may have a visual/optical axis 10.

Figure 1B:
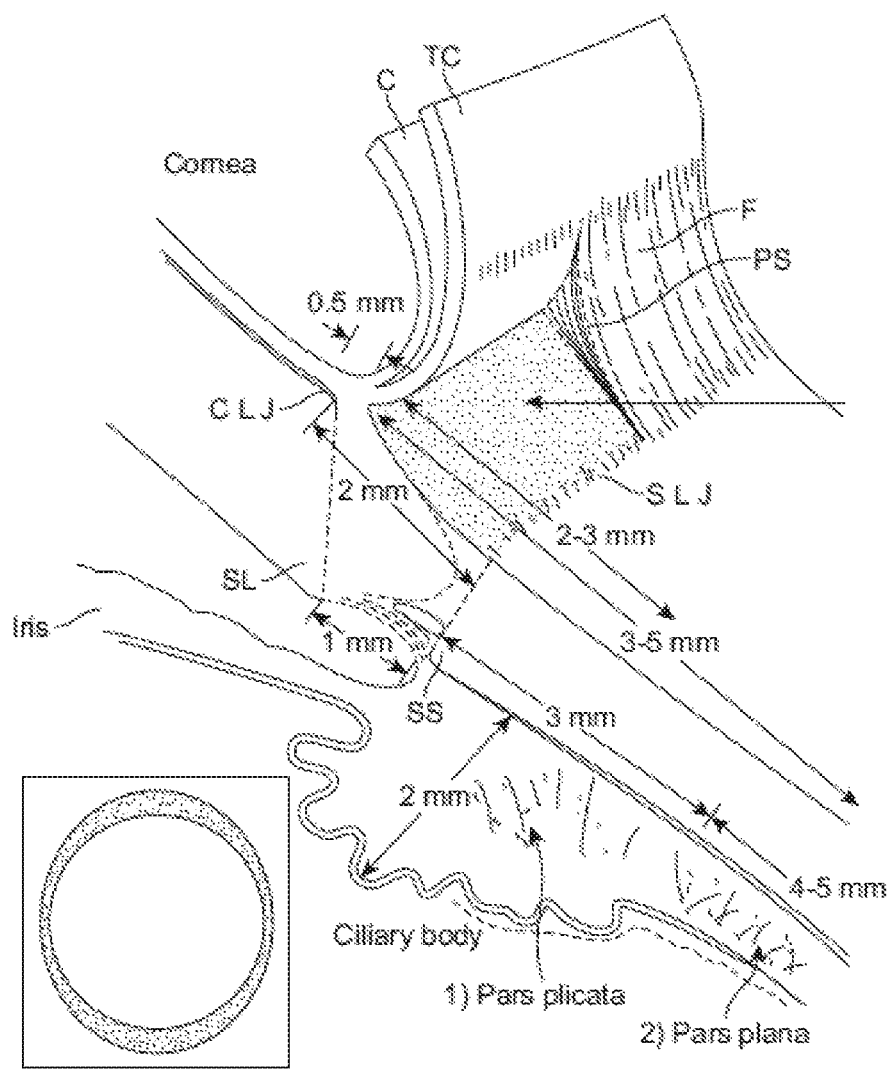
FIG. 1B shows further details of the surgical eye anatomy.

FIG. 1B shows further details of the surgical eye anatomy. Embodiments described herein may target intraocular structures that span from the posterior pars plicata to the pars plana. Alternatively, the pars plana may be targeted and the pars plicata, ciliary body, and other ciliary processes avoided.

Figure 2A:
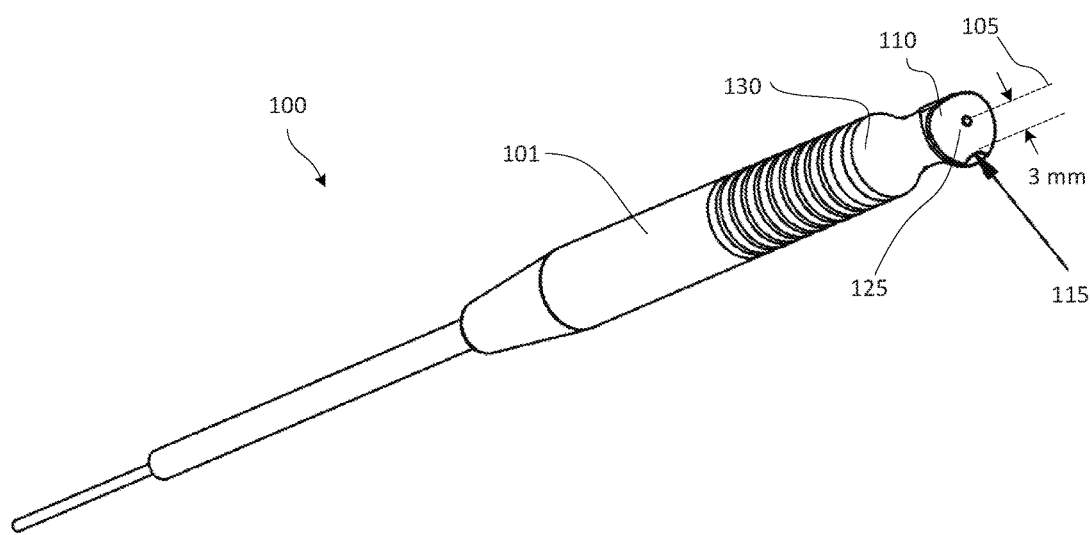
FIGS. 2A-2D illustrate an exemplary treatment probe according to some embodiments.
Figure 2B:
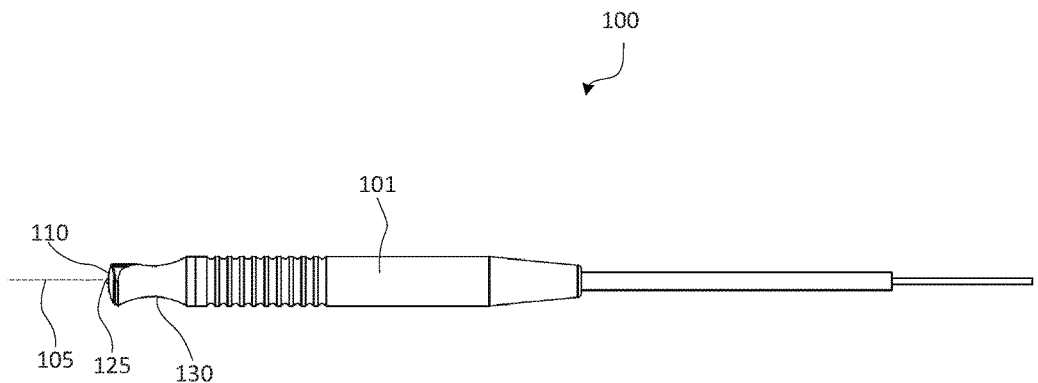
Figure 2C:
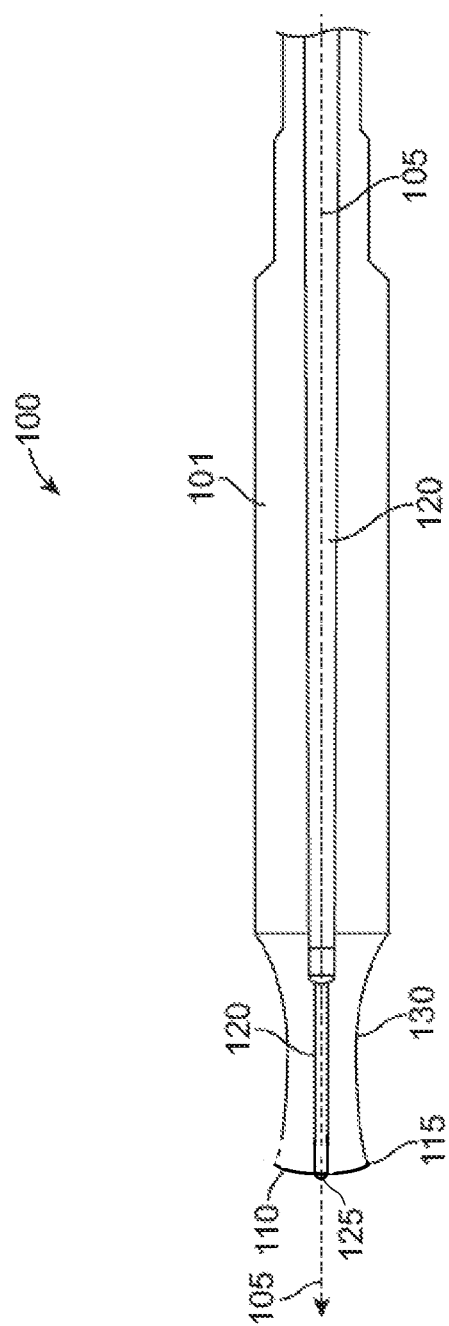

In embodiments of the present invention, a laser energy delivery handpiece is provided that is specifically designed for the efficient transconjunctival/transscleral delivery of laser energy, for example, infrared laser energy from a pulsed 810 nm diode laser, over the posterior region of the pars plicata, over the pars plana-pars plicata junction, and/or over the pars plana. Optical energy from other sources, for example, light emitting diodes (LEDs), may be delivered as well. FIGS. 2A-2D show an exemplary handpiece 100 for lowering pressure of an eye. FIG. 2A provides an isometric view of the exemplary handpiece 100. FIG. 2B provides a side view of the exemplary handpiece 100. Laser energy delivery handpiece 100 comprises an elongate body 101 and an end portion/contact member 130 disposed on one end of the elongate body 101. Laser energy delivery handpiece 100 defines a treatment axis 105 for delivering laser energy to a patient's eye 1. End portion 130 of the laser energy delivery handpiece 100 defines a contact surface 110.

In some embodiments of the present invention, the laser energy delivery handpiece 100 has a proximal input end, a distal output end, a top, a bottom and sides. Elongate body 101 may be adapted to receive and/or enclose a fiber optic 120 along the treatment axis 105, as shown more clearly in the cross-sectional image of handpiece 100 of FIG. 2C. The distal end 125 of the fiber optic 120 may terminate at the contact surface 110. In various embodiments, the distal end (output tip) 125 may protrude from 0.25 mm to 1.0 mm, preferably 0.4 mm, beyond the contact surface 110. In some embodiments, the distal end 125 protrudes and terminates at a hemispherical tip. The indentation of the output tip 125 may increase the transmission of infrared laser energy through the conjunctiva and sclera by compressing these tissues.

Figure 2D:
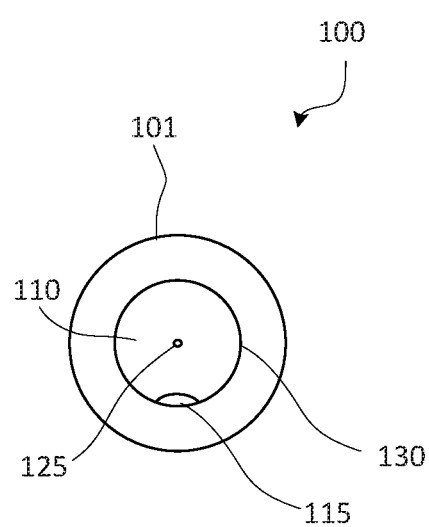

A contact surface 110 of the handpiece 100 may be designed so that a fiber optic 120 coupled to the handpiece 100 may have a hemispherical tip 125 that is about 1-5 mm (e.g., 3 mm, 3.4 mm, or the like) from an edge of the contact surface 110. In some embodiments, the footprint of the contact surface 110 may identify the position of a protruding hemispherical laser beam output tip 125, or other non-blunt geometry, with respect to a reference feature 115. In some embodiments, the contact surface 110 may include a reference feature 115 (e.g., a limbal placement edge) for aligning the output tip 125 of treatment probe 100 with the a target region of the eye 1. For example, as shown in FIG. 2D, the front view of handpiece 100, contoured surface 110 comprises a generally round perimeter surface face with a diameter between 5-8 mm and a limbal placement edge 115. A limbal placement edge 115 may be provided to align the output tip 125 with reference to the limbus of the eye. Limbal placement edge 115 may be a concave arc and have a contact surface contour that conforms to the limbus and is generally circularly concave with a radius of at least 5 mm to permit close apposition to the limbus. Accordingly, in some embodiments, the output tip 125 may be about 1-5 mm (e.g., 3 mm, 3.4 mm, or the like) from an edge of the reference feature 115. Once aligned, the output tip 125 may facilitate the optimal irradiation over the eye's pars plana-pars plicata junction and/or over the eye's pars plana, from the limbus. For example, once aligned, output tip 125 may provide treatment 1-5 mm posterior to the limbus at any 360° location, when in normal contact with the conjunctiva/sclera and with the reference feature 115 or an edge of the contact surface 110 aligned with the limbus, in particular, the outer edge of the limbus.

Optionally, contact surface 110 may have a rounded perimeter surface such that it does not conform to the shape of the sclera at the limbus when the axis 105 of the handpiece 100 forms a predetermined angle relative to the optical axis 10 of the eye 1. For example, the contact surface 110 may have a convex configuration. A convex and/or rounded perimeter surface configuration of contact surface 110 may advantageously facilitate smooth sweeping of the handpiece 100 over the target regions of the eye 1 during treatment. Additionally, a distal end of the treatment fiber optic that does not protrude by more than 0.4 mm from the convex contact surface may also facilitate smooth sweeping of the handpiece 100 over the target regions of the eye 1 during treatment. The contact surface 110 may have a single radius of curvature across the contact surface 110 and no sharp edges. For example, the radius of curvature for the convex configuration may range from 5-50 mm. Further the edges of the contact surface 110 may also be rounded. For example, the edge between the contact surface 110 and the end portion 130 may be rounded so as to provide a smooth transition between the surfaces. Such features may facilitate sliding of the handpiece 100 over the target regions of the eye. These features may be in direct contrast to previous devices where the contact surface was generally concave so as to conform to the sclera of the eye. Additionally, prior devices utilized edges that may indent the surface of the eye to provide a reference to facilitate repositioning of the probe. Such configurations make sweeping the probe across the eye more difficult as the probe edges of the concave surface may catch on the tissue of the eye. Further, in contrast to devices which utilize concave contact surfaces and indentation edges for precise and consistent treatment delivery, the convex contact surface feature of some embodiments may facilitate some variability in the treatment delivery. For example, with a contact surface that does not conform to the shape of the eye, a laser treatment position posterior to the limbus may vary when the treatment probe is slid along the surface of the eye in one or more passes or sweeps. Also, an angle of treatment laser delivery may also vary when a treatment probe is slid along the surface of the eye when the probe has a non-conforming contact surface (e.g., a convex contact surface). Surprisingly, it may be beneficial to introduce variability in treatment position and/or angle when sliding the treatment probe along the surface of the eye.

The footprint contact surface 110 is designed to allow the surgeon to administer the treatment either with a series of individual applications with precisely defined angular spacing or radial displacements about the optical axis of the eye and/or with a continuously sliding motion about the optical axis of the eye and over the conjunctiva overlying the pars plana (e.g., 120° sliding motion, 150° sliding motion, 180° sliding motion, 360° sliding motion, or the like), each of which are described in further detail below. As discussed above, the sliding motion may introduce beneficial variability in the position of the pulsed laser energy and delivery angle relative to the optical axis of the eye.

Figure 3A:
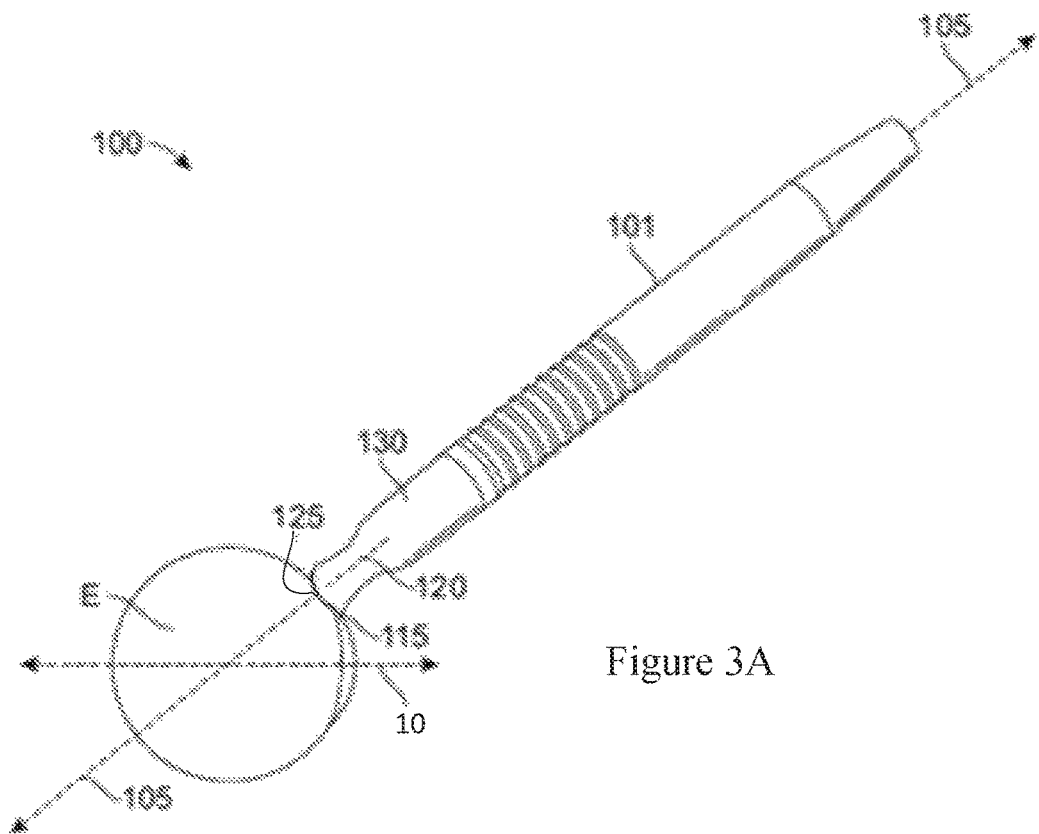
FIG. 3A-3E show an exemplary method of using laser eye delivery handpiece 100 to delivery laser energy to treat an eye.

FIGS. 3A-3E show an exemplary method of using laser eye delivery handpiece 100 to delivery laser energy to treat an eye. As shown in FIG. 3A, the laser energy delivery handpiece 100 may be positioned against the eye E with the concave limbal arc reference 115 next to the limbus and directing the laser energy radially to the eyeball center over the pars plana-pars plicata junction, generally indicated by the axis 105. Alternatively, the distance between short limbal placement edge 115 and tip 125 will be such that the laser energy is directed to the eyeball center over the pars-plana or any structure posterior the limbus. In this position, handpiece 100 is at a first treatment site so that contoured surface 110 is in contact with the sclera of the eye E and concave limbal arc reference 115 is in contact with the limbus, the region of the eye between the cornea and the sclera. Treatment axis 105, as defined by handpiece 100, forms a predetermined angle, for example, a 40° degree angle, with optical axis 10 of the eye E. Tip or opening 125 is spaced posterior the limbus with a distance which may be, for example, about 3 mm. Laser energy is directed through tip or opening 125 to direct laser energy to the pars plana.

In an exemplary embodiment, the directed laser energy comprises pulsed laser energy from an infrared laser that can be operated in pulsed, as well as continuous wave emission modes. For example, the pulsed continuous wave infrared laser may have about a 30% duty cycle, with an "on" time of about 500 µs and an "off" time of about 1100 µs, about a 15% duty cycle, with an "on" time of about 300 µs and an "off" time of about 1700 µs, or about a 10% duty cycle, with an "on" time of about 200 µs and an "off" time of about 1800 µs. Careful selection of the laser energy pulse "on" and "off" times can avoid undesired thermal damage to a target by allowing the target to cool during the "off" time of the laser before the next pulse of laser energy is delivered during the "on" time. The duty cycle and "off time" may be selected so that cumulative thermal buildup, caused by insufficient cooling during the "off" time of the laser beam, is avoided. Thus, laser damage can be reduced to a minimum level sufficient to trigger a biological response needed for lowering of intraocular pressure (IOP).

In some continuous sliding motion applications, it may be preferable if the duty cycle is a duty cycle between a 15% duty cycle and a 45% duty cycle, for example about 30% with an "on" time of about 500 µs and an "off" time of about 1100 µs. These duty cycle ranges may be particularly advantageous for transscleral energy delivery and offer particularly surprising therapeutic results after energy delivery in a continuous sliding motion.

In the exemplary procedure described with reference to FIGS. 3A-3E, a duty cycle of 15% may be used. The power of the laser may be set at 1500 mW and the pulse envelope "on" time may be 300 ms.

Figure 3B:
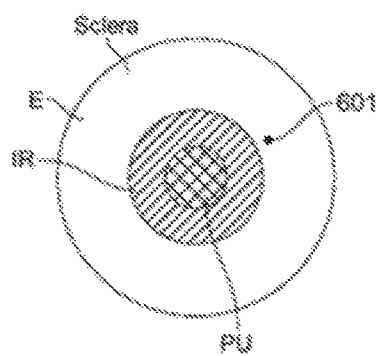

As shown in FIG. 3B, laser energy is directed toward a first application site 601 posterior to the limbus. Afterwards, handpiece 100 is lifted and repositioned, to a second treatment region adjacent the first treatment region. Further, handpiece 100 may be rotated so that at the second position, handpiece 100 is again positioned so that concave limbal arc reference 125 is adjacent the limbus.

Figure 3E:
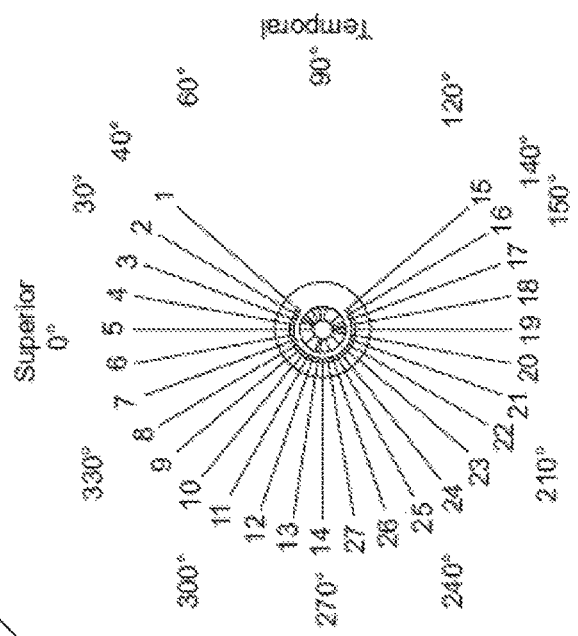
Figure 3C:
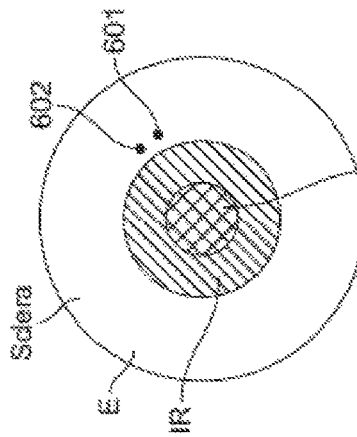
Figure 3D:
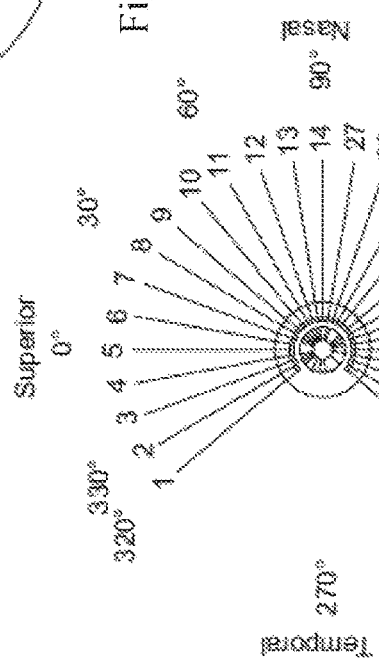

As shown in FIG. 3C, laser energy is directed toward a second application site 602. Thus, first site 601 and second site 602 are equidistant from the optical axis 10 of the eye E. This process of repositioning handpiece 100 and directing laser energy toward the pars plana is repeated for a third spot, a fourth spot, and so forth. For example, as shown in FIG. 3D, laser energy is directed toward a first treatment site at 320° on a right eye, then toward a second treatment site at 330°, and then successively clockwise every 10° until a site at 90°, e.g., toward sites at 340°, 350°, 360°, 10°, 20°, 30°, 40°, 50°, 60°, 70°, 80°, and then 90°, thereby creating a first 130° arc of treatment sites on the superior side of the eye E. Thus, a series of individual applications with precisely defined angular spacing or radial displacements are made. A second 130° arc of treatment sites on the inferior side of the eye E may then be created, starting from directing laser energy toward the site at 220° and then toward successively counter-clockwise sites every 10° until a site at 100°. Upon completion of laser treatment, an arc equidistant from the limbus and of approximately 270° will have received discrete laser exposures.

As shown in FIG. 3E, a similar procedure of directing laser energy toward a plurality of treatment points can be made on the left eye. Laser energy is directed toward a point at 40° and then successively counterclockwise until a point at 270°, creating a first 130° arc of treatment points. Then, laser energy can be directed toward a point at 140° and then successively clockwise every 10° until a point at 260°. In some embodiments, laser energy may be exposed to each point for about 1.0 seconds at a power of 1.5 W. The duty cycle of the laser energy may be 10%, with an "on" time of about 200 µs and an "off" time of about 1800 µs for each pulse of a train of about 500 pulses delivered to each application site with about 1.0 second exposure durations. The eye E may also be treated at more or less treatment points at different areas, for example, the eye E may be treated so that a superior arc and an inferior arc of each of 150° or even 180° can be created. For example, 20 stationary applications over 360° may be made, with 5 stationary applications per quadrant. Treatment points may also be alternatively spaced apart from each other by other angles besides 10°, for example, by providing handpieces with different distances between edges 160.

In a preferred treatment, 5 clock hours of the eye superior to the equator and 5 clock hours inferior to the equator are treated. As mentioned above, in some embodiments, the footprint contact surface 110 may be slid around the treatment area while the laser continuously delivers pulses of laser energy as opposed to individual spaced applications described in the previous embodiment. The continuously emitted laser energy that is delivered while the footprint contact surface slides over the sclera can be seen as paint delivered with a sliding brush. When applied ab-externo with a continuously sliding motion and reversal of direction as necessary, a portion or all of the upper 180° of the eye may be treated in one continuous exposure. Multiple reversals of direction to reirradiate tissue just treated may be a technique that helps avoid excessive build-up of heat in these tissues while enhancing the therapeutic efficacy by irradiating a wider line of tissue. Similarly, the lower 180° of the eye may be treated in a second such exposure. In another move, a low power pulse laser emission may be "painted" over the intended structures, for example, the ciliary body. This provides an irradiation for all pigmented cells in a movement analogous to a paintbrush of photothermal energy sweeping over the scleral surface with sweeping time and rate determined by the surgeon.

Figure 4A:
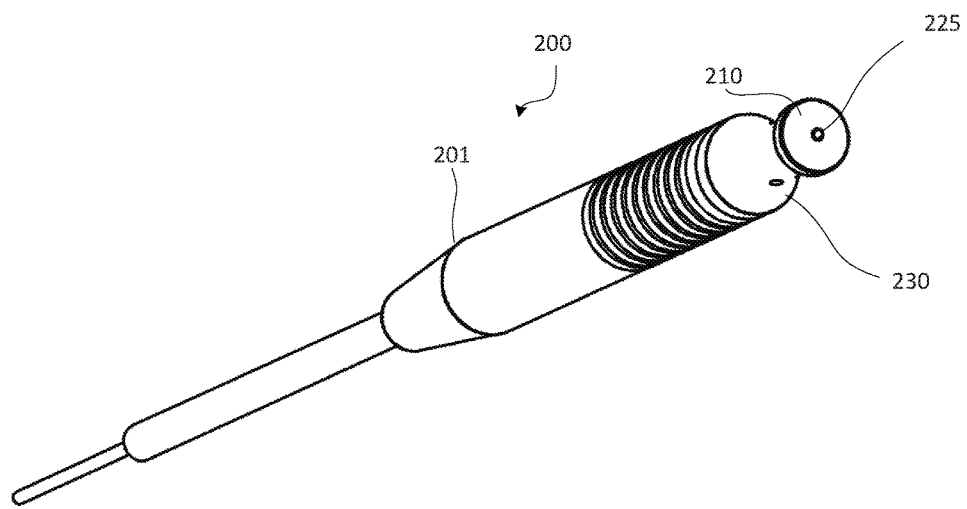
FIG. 4A-4C illustrate another exemplary handpiece according to further embodiments of the invention.
Figure 4B:
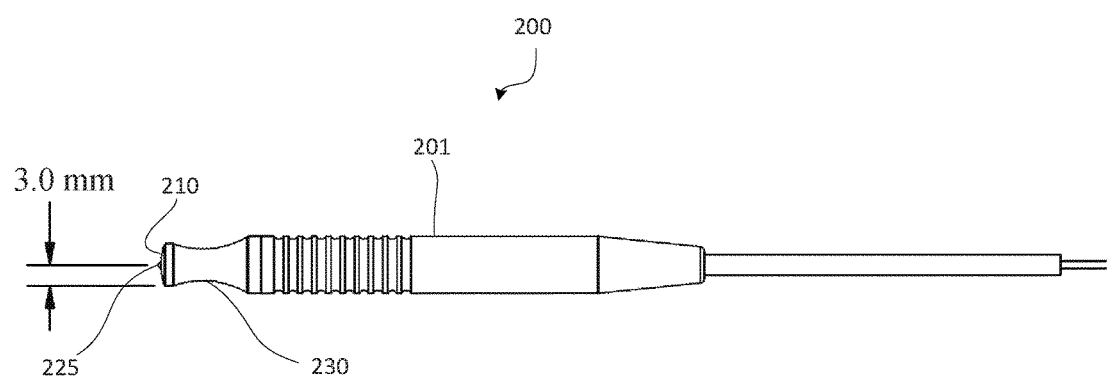
Figure 4C:
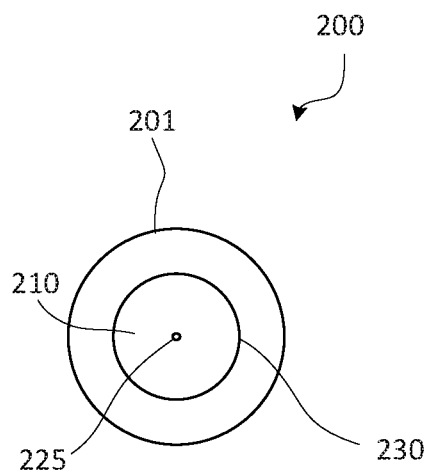

FIGS. 4A-4C illustrate another exemplary handpiece 200. Exemplary handpiece 200 is similar to exemplary handpiece 100. As can be seen in the isometric view of FIG. 4A and the side view of FIG. 4B, handpiece 200 may include an elongate body 201 and an end portion/contact member 230 disposed on the distal end of elongate body 201. End portion/contact member 230 comprises a convex contact or other contact surface 210 that does not conform to the shape of the sclera. Advantageously, the convex configuration of the contact surface 210 may facilitate sliding of the probe along the surface of the eye. The elongate body 201 may house a treatment fiber 220. A distal end 225 of treatment fiber 220 may terminate at the convex contact surface 210. Accordingly, handpiece 200 is similar to exemplary handpiece 100 except that limbal feature 115 has been removed. When using the embodiments illustrated in FIGS. 2A-2D, the probe may require simultaneous rotation of the probe about the axis 105 when repositioning or sweeping it along the surface of the eye during laser delivery in order to maintain its alignment with the limbus. In contrast, when using the embodiments illustrated in FIGS. 4A-4C, where the limbal alignment feature has been removed, and the tip is now a full circle whose radius is the intended spacing from the limbus as shown more clearly in front view provided by FIG. 4C. In some embodiments, the spacing may be 1-5 mm, (e.g., 3 mm, 3.4 mm, or the like). Removing the limbal alignment feature eliminates the requirement for rotating the probe about the axis 105 in synchrony with the sweeping motion used during laser delivery, thereby simplifying the treatment.

Figure 5A:
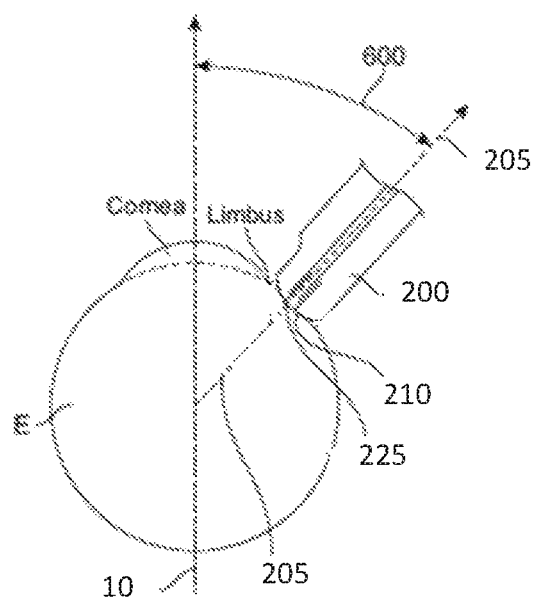
FIG. 5A-5C illustrate an exemplary method of treating an eye using probe and delivering laser energy in a sweeping motion.
Figure 5B:
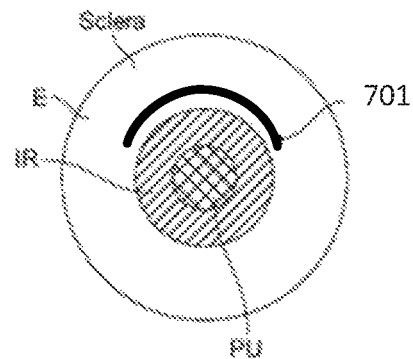
Figure 5C:
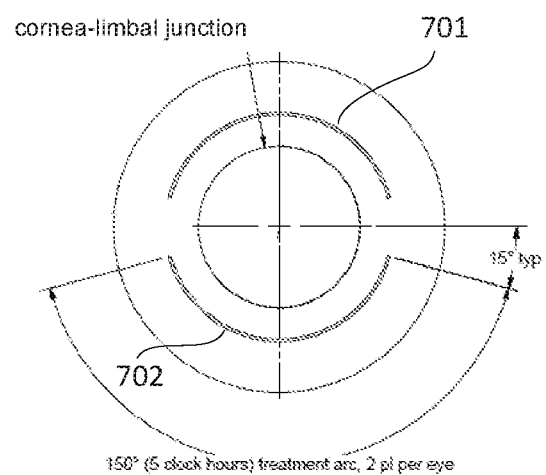

FIG. 5A-5C illustrate an exemplary method of treating an eye using probe 200 and delivering in a sweeping motion. Tip 210 may first be positioned about 3 mm posterior the limbus and then gradually slid in an arc motion while exposing the targeted region of the eye (e.g., the pars plana) to pulsed laser energy. Such a method may create a treatment region 701 as illustrated in FIG. 5B.

The treatment region may be a 180° arc or less in some embodiments. For example, a probe may be slid in a 100° to 160° arc motion. Optionally, the arc motion may start at the 10 o'clock or 300° position of the eye and be swept to the 2 o'clock or 60° position, all the while exposing the targeted region of the eye, e.g., the pars plana, to pulsed laser energy. In some embodiments, a superior treatment arc of 150° can be created and an inferior treatment arc of 150° may be created. The inferior treatment arc 702 shown in FIG. 5C may be created by positioning tip 225 about 3 mm posterior the limbus at the 8 o'clock position or 240° position and gradually sliding handpiece 200 until the tip 225 reaches the 4 o'clock position or 120°, all the while exposing the targeted region of the eye, e.g., the pars plana, with pulsed laser energy. Optionally, treatment arcs may be formed by a number of short strokes or incremental sweeps. For example, shorter incremental sweeps (e.g., 30°, 45°, 40°, 45°, 50°, 55°, 60° or the like) may be used to form full treatment arcs of a desired length (e.g., 100°, 120°, 150°, 180°, or the like).

Figure 7:
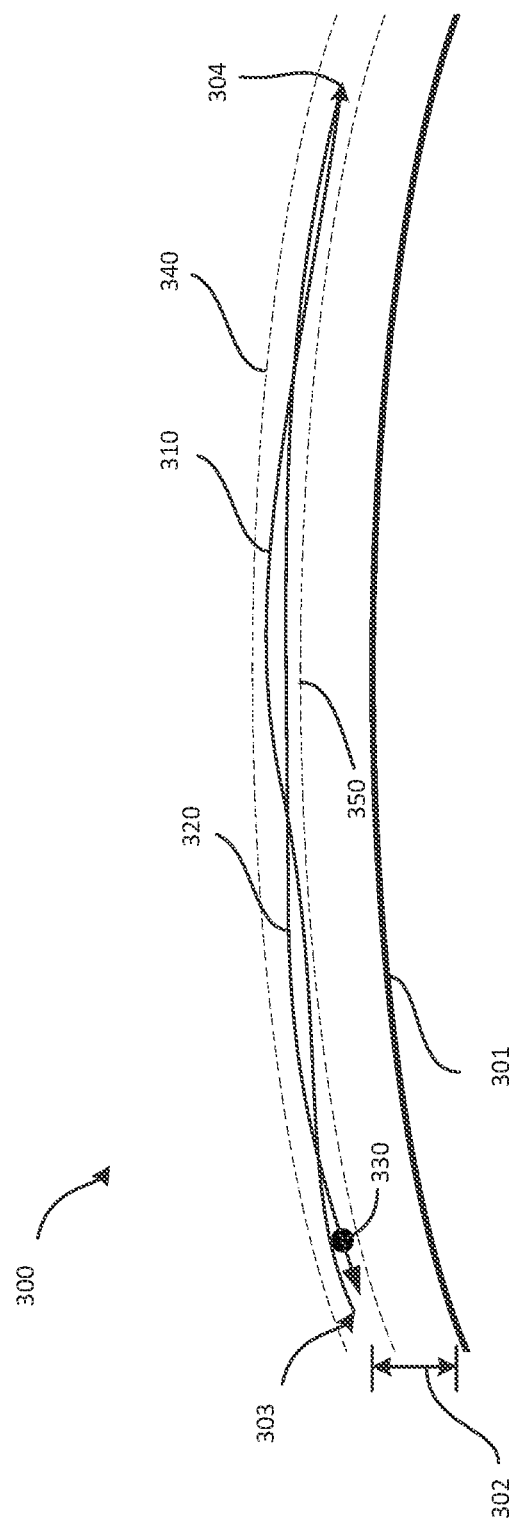
FIG. 7 shows exemplary treatment sliding paths along the surface of the eye according to some embodiments.

As discussed above, use of a convex contact surface and a sliding treatment delivery technique may beneficially add variability in the treatment position and angle as the treatment probe is slid along the surface of the eye in one or more traverses. FIG. 7 illustrates exemplary treatment region eye 300 an eye treated by a first sweep 310 and a second sweep 320. The treatment region 300 is generally spaced apart from limbus 301 by a distance 302. Distance 302 may be between 2.5-3.5 mm. First sweep 310 may start at position 303 and travel along a first path to position 304. Thereafter, the treatment probe may be slid back towards position 303 along a second path along treatment region 300 to create second sweep 320. As illustrated the path of the first sweep 310 and the path of the second sweep 320 are variable as the treatment probe is swept between position 303 and position 304. While illustrated with two sweeps 310, 320, it should be understood that in some embodiments a single sweep may be sufficient. Further, in other embodiments, 3-12 sweeps (e.g., 5-10 sweeps or so) may be performed along a treatment region 300 for delivery of laser energy into the eye.

Additionally, spot 330 illustrates an exemplary treatment spot size of a treatment probe. Due to the treatment spot size and the variability in treatment sweep positions and/or angles, a treatment zone 300 may have an expanded treatment upper boundary 340 and an expanded treatment lower boundary 350.

In exemplary embodiments, the duration of laser energy exposure for each treatment arc may be 30-60 seconds (e.g., 45-55 seconds, 50 second, or the like). In some embodiments, several traverses of the arc motion may be completed during the duration of laser energy exposure. For example, in some embodiments 1-20 traverses in the arc motion may be completed during the duration of laser energy exposure. In some embodiments it may be preferable to complete approximately 5-10 traverses of an approximately 150° arc motion during a 50 second duration of laser energy exposure. Based on estimates for average adult human eye anatomy of 12.3 mm globe radius and 6 mm limbal radius, then an arc of laser treated tissue positioned 3 mm posterior to the limbus and covering an angle of 150° (e.g., 5 clock-hours) may be approximately 22 mm in length. Sweeping over this arc 5 times, for example, represents a total length of 110 mm. If this representative length is treated in 50 seconds, say, then this represents a linear sweep speed of about 110/50=2.2 mm/s. A fiber optic tip of 0.6 mm diameter will therefore be directly irradiating tissue directly below it for only approximately 0.6/2.2=0.27 s. This "dwell time" is approximately an order of magnitude less than the multi-second (often 2-5 seconds) cyclophotocoagulation dwell times typically used for coagulative destruction of ciliary tissue. This short dwell time helps reduce or eliminate excessive tissue temperatures that can result in tissue necrosis or even disruptive "pops" due to boiling of subsurface ocular tissue. It also helps explain the milder tissue effects and postoperative symptoms typically associated with this treatment hardware and techniques vs. other cyclodestructive procedures. The sweeping technique also imposes a more uniform time-temperature profile on ocular tissue than is possible to achieve using the "pick, place, and dwell" technique common to other cyclodestructive procedures. Long exposures to static targets can results in on-axis tissues that are overtreated with excessive temperature excursions (sometimes to the point of necrosis), nearby tissues that receive a more optimal thermal profile, and more peripheral tissues that are less optimally treated.

The peak power of the laser may be 2 watts. A total of 31,250 pulses at a rate of 625 pulses per second may be made during an exposure of 50 seconds duration. Each pulse may have an energy of 1.0 mJ. This represents energy delivery at a rate of 625 mJ/s, or an average power of 0.625 W. This value contrasts significantly when compared with the laser power setting of 1.5 to 2.5 W typically used with other cyclodestructive techniques. Like the sweeping technique described earlier, this lower average power setting also helps reduce the peak temperatures imposed on target tissues during laser treatment and avoids unnecessary tissue destruction.

While the method of sweeping the treatment area during delivery of the treatment laser is discussed and illustrated as using treatment probe 200, it should be understood that other configurations are possible, such as the treatment probe 100.

Figure 8:
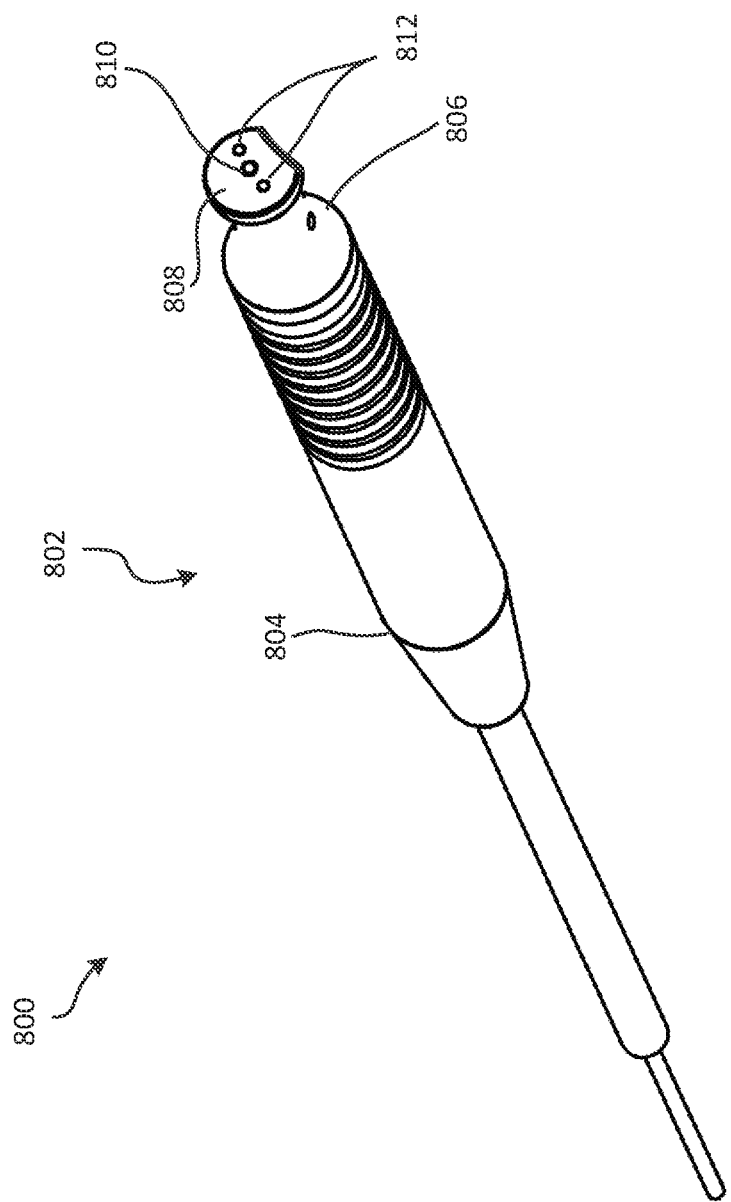
FIG. 8 shows an exemplary embodiment including a illumination light fiber for illuminating a target tissue of the eye.

FIG. 8 illustrates an exemplary illuminated treatment probe according to some embodiments of the invention. The treatment probe 800 may include an elongate body 802 defining a handle having a proximal end 804 and a distal end 806. The distal end 806 of the elongate body 802 may include a convex contact surface 808 for sweeping or sliding along a surface of the eye. A treatment fiber may extend along the elongate body 802 and be configured for delivering a treatment laser to the eye from a distal end 810 of the treatment fiber. The treatment probe 800 may further include one or more illumination light conduits for delivering illuminating light to the eye from a distal end 812 of the illumination light conduit. An edge of the ciliary process of the eye may be illuminated by directing illuminating light from the distal end of the illumination light conduit of the treatment probe 800 to the eye. Advantageously, the distal end 810 of the treatment fiber of the treatment probe 800 may be positioned per the illuminated edge of the ciliary process during the sweeping process. Methods of treatment laser delivery may include delivering the treatment laser to the eye from the distal end of the treatment fiber while the treatment probe 800 is positioned per the illuminated edge of the ciliary process.

Optionally, embodiments may have light conduits that extend from the distal end 806 of the elongate body 802 for directing illumination light to other portions of the eye. For example, the edge of the ciliary process of the eye may be illuminated by delivering illumination light at an angle ranging from 30-60° from the visual axis of the eye. In some embodiments, the edge of the ciliary process of the eye may be illuminated by delivering illumination light through the cornea and parallel to the visual axis of the eye of the patient. Optionally, the illumination light may be delivered through the pupil of the eye of the patient. In some embodiments, the edge of the ciliary process of the eye may be illuminated by delivering illumination light through the cornea directly at the angle of the anterior chamber.

Devices may use optical waveguides, fiber optics, light guides, light tubes, or the like to deliver illumination light at preferred angles and positions. In some embodiments, a distal end of the light conduit may be repositionable (manually and/or mechanically) to deliver light at various angles relative to the eye and/or to different regions of the eye. Accordingly, some embodiments may be used for patients with different sized eyes or needs. Thus, in some embodiments, the method may include adjusting the distal end of the illumination light conduit to a configuration suitable for the patient.

In some embodiments, the distal end of the illumination light conduit may terminate at the contact surface of the treatment probe. In some embodiments, the illumination the light conduit may branch out such that the illumination light conduit comprises a first distal end and a second distal end for delivering illumination light from a plurality of points. The first distal end and the second distal end of the illumination light conduit may terminate on both sides of the distal end of the treatment fiber such that illumination light is directed in the same plane as the treatment laser.

In some embodiments, a system for treating an eye of a patient for glaucoma is provided. The system may include a console for generating a treatment laser for treating the eye and for generating an illumination light for illuminating the ciliary body of the eye. The system may further include a treatment probe configured to operatively couple with the console to deliver the treatment laser and the illumination light from the console toward the eye of the patient. The treatment probe may include an elongate body defining a handle having a proximal end and a distal end. A treatment fiber may be housed in the elongate body and configured for delivering a treatment laser to the eye from a distal end of the treatment fiber. An illumination light conduit may be housed in the elongate body and configured for delivering illuminating light to the eye from a distal end of the illumination light conduit. The treatment probe may further include a convex contact surface for sweeping along a surface of the eye.

In yet another embodiment, a treatment probe for treating an eye of a patient for glaucoma may be provided. The treatment probe may comprise an elongate body defining a handle having a proximal end and a distal end. A light source may be housed in the elongate body and have a light transmitting surface oriented for delivering a treatment beam to the eye from the distal end of the elongate body. The treatment probe may also include an illumination light source housed in the elongate body and configured for delivering illuminating light to the eye from a distal end of the body. For example, a treatment probe may house one or more laser diodes, one or more light emitting diodes, or combinations thereof for providing illumination light and treatment light to an eye.

EXPERIMENTAL SECTION

Experiment A

An initial study using a handpiece with a contact probe similar to those described above was conducted at the National University Hospital in Singapore. In the study, treatment procedures similar to those described above were conducted on a number of glaucomatous eyes. This initial study tracks glaucomatous eyes for about 6 months, the treated eyes being treated with the aforementioned handpiece and a treatment procedure using pulsed laser energy.

Patients with advanced glaucoma refractory to maximum tolerated medical and surgical treatment and a visual acuity of worse than 6/60 were included in the study. Patients with recent eye surgery within 3 months of enrollment, active ocular inflammation or inability to give informed consent were excluded.

The procedure was performed by a single surgeon to patients under local anesthesia. The contact probe was designed for accurate positioning of a fiber optic at 3.0 mm behind the limbus of the eye.

The laser settings were 2000 mW, applied over a total duration of 100 s, with a pulse duration of 0.5 ms and a pulse interval of 1.1 ms. Shots were applied over 360° avoiding the 3 o'clock and 9 o'clock regions and any areas of thinning.

The main outcome measure was success of treatment, defined as a 30% or more reduction of IOP from baseline or an IOP of less than 21 mm Hg at 6 month follow-up.

23 eyes of 23 patients were treated. The patients had a mean age of 62.9±20.3 years. The mean duration of follow-up was 5.3±1.5 months. The mean pre-treatment IOP was 37.1±9.5 mm Hg.

TABLE 1 below summarizes mean IOP before and after treatment at 1 day, 1 week, 1 month, 3 months, and 6 months post-op. All mean post-treatment IOPs were significantly lower than the pre-treatment IOPs (paired Student's t-test, $p<0.001$).

TABLE 1

POST-OP IOP MEASUREMENTS

| Time Point | Mean IOP (mmHg) | Mean IOP Reduction (%) |
| --- | --- | --- |
| Baseline | 37.1 ± 9.5 | — |
| 1 day post-op | 28.7 ± 10.8 | 24.0 ± 17.1 |
| 1 week post-op | 25.6 ± 9.8 | 30.9 ± 18.7 |
| 1 month post-op | 22.2 ± 7.0 | 38.2 ± 19.6 |
| 3 months post-op | 22.9 ± 8.9 | 35.4 ± 24.2 |
| 6 months post-op | 23.7 ± 9.7 | 37.6 ± 19.4 |

Success of the treatment was defined as a 30% or more reduction from baseline or a final IOP of less than 21 mm Hg at the $6^{th}$ month follow-up visit. The success rate was 38% at 1 day, 57% at 1 week, 76% at 1 month, 80% at 3 months and 69% at 6 months. None of the patients had hypotony or loss in their best corrected visual acuity.

Experiment B

A similar study using a handpiece with a contact probe similar to those described above was conducted also at the National University Hospital in Singapore. In the study, treatment procedures using pulsed laser energy similar to those described above were conducted on a number of glaucomatous eyes. This study tracks the treated eyes for up to 18 months.

The MicroPulse™ procedure was performed by a single surgeon in the outpatient setting. Regional anesthesia with peribulbar or retrobulbar injection of 2% lidocaine was given prior to the procedure. Scleral transillumination was used to identify the position of the ciliary body as well as any areas of thinning. A diode laser emitting ball-lens tip contact probe, which is similar to those described above, was applied axially at the limbus. This probe housed a quartz fiberoptic of 600 μm in diameter. Its end protrudes 0.7 mm from the handpiece. The probe was specifically designed to allow positioning of the fiberoptic at 3.0 mm behind the surgical limbus, i.e., the distance from the reference edge of the contact surface of the probe to the fiberoptic was 3 mm. The laser settings were 2000 mW, over a total duration of 100 s, with a train of repetitive pulses each with a pulse duration of 0.5 ms and a pulse interval of 1.1 ms. The treatment was applied by "painting" or uniformly sliding the probe over 360°, avoiding the 3 and 9 o'clock meridians and any area of thinned sclera. Total energy delivered to the ciliary body was 60-90 J.

The amount of intraoperative pain experienced by the patient was recorded and additional regional anesthesia was administered as required. Postoperatively, topical predniso-lone acetate 1% was prescribed four times daily along with oral mefenamic acid for 5 days. Follow-up examinations were performed at 1 day, 1 week, 1 month, 3 months, 6 months, 12 months, and 18 months. Pain scoring, visual acuity, Goldman applanation tonometry, slit lamp biomi-croscopy and dilated fundus examinations were carried out at every visit. Retreatment over 360 degrees was performed between 1 to 3 months if IOP reduction was less than 20%.

Statistical analysis was performed using SPSS software version 15.0. Means were compared using the two-tailed paired Student's t-test, with $p<0.05$ being considered significant.

46 eyes of 44 patients were evaluated in this study. The mean age of the patients was 63.2±16.0 years. There were 36 men (81.8%). Right eyes of 17 (38.6%) patients, left eyes of 23 (52.3%) patients and both eyes of 2 patients underwent treatment with MicroPulse™ TSCPC. TABLE 2 below shows the distribution of glaucoma diagnoses. Four eyes received retreatment between 1 to 3 months after the initial laser.

TABLE 2

DISTRIBUTION OF GLAUCOMA DIAGNOSES

| Type of Glaucoma | No. (%) |
|---|---|
| Neovascular glaucoma | 17 (38.6%) |
| Primary open angle glaucoma | 10 (22.7%) |
| Primary angle closure glaucoma | 10 (22.7%) |
| Others | 7 (16.0%) |

TABLE 3 below summarizes mean IOP before and after treatment at 1 day, 1 week, 1 month, 3 months, 6 months, 12 months, and 18 months post-op. All mean post-treatment IOPs were significantly lower than the pre-treatment IOPs (paired Student's t-test, $p<0.001$). The mean duration of follow-up was $16.2\pm4.5$ months.

TABLE 3

POST-OP IOP MEASUREMENTS

| Time Point | Mean IO (mmHg) | Mean reduction in IOP from baseline (%) |
|---|---|---|
| Baseline | 39.1 ± 12.7 | — |
| 1 day | 31.1 ± 13.5 | 21.6 |
| 1 week | 28.1 ± 12.1 | 28.1 |
| 1 month | 27.6 ± 12.8 | 28.4 |
| 3 months | 27.2 ± 12.8 | 23.5 |
| 6 months | 26.0 ± 13.4 | 27.2 |
| 12 months | 26.5 ± 12.6 | 27.3 |
| 18 months | 26.9 ± 11.8 | 30.5 |

Figure 6:
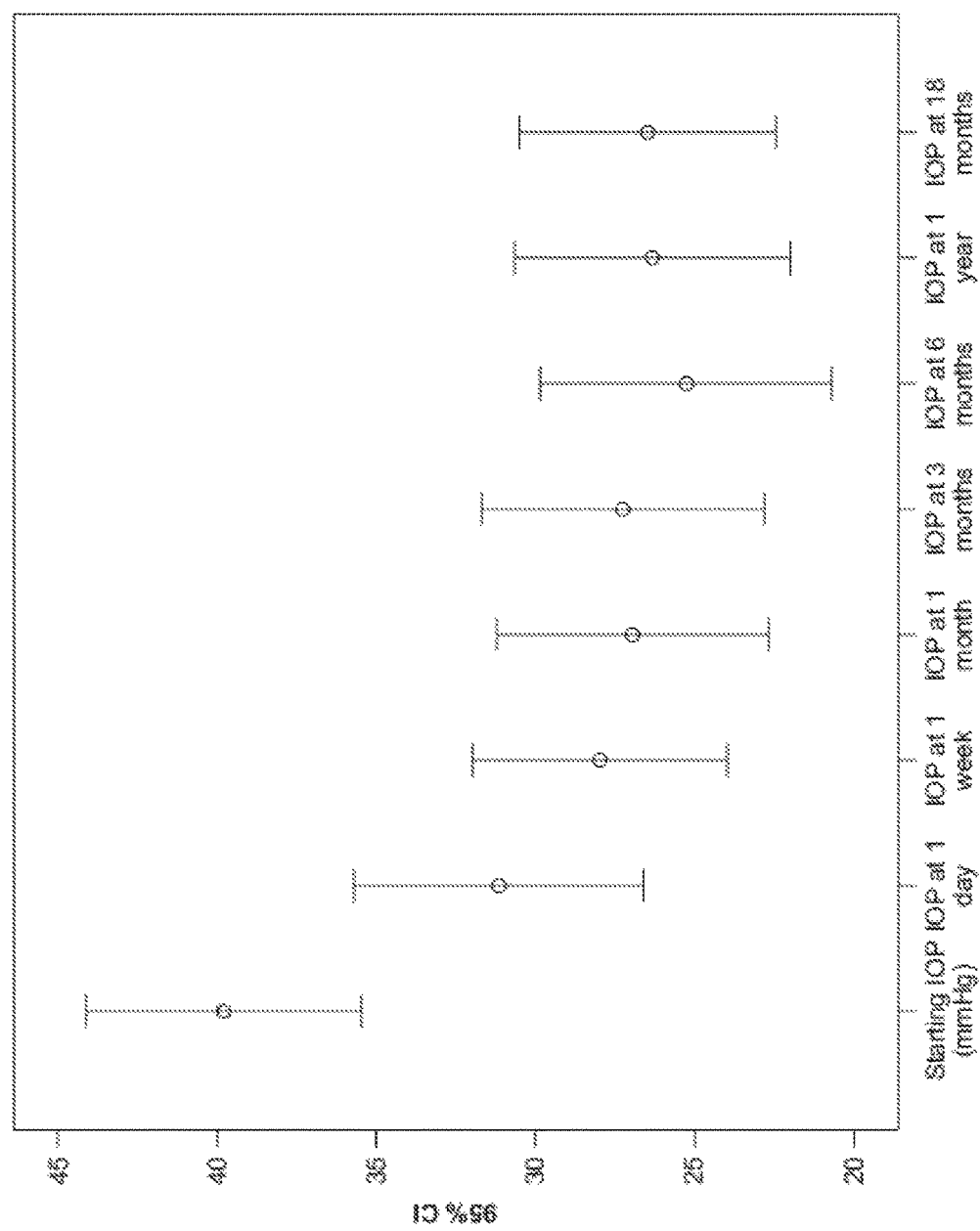
FIG. 6 shows the decrease in IOP after an exemplary treatment over 6 months.

As shown in FIG. 6, the decrease in IOP appears to be gradual and sustained over 6 months. All patients who required systematic acetazolamide (n=6) prior to the treatment were able to discontinue the drug by the first postoperative day. The mean number of topical anti-glaucoma medication was reduced from 1.8±1.1 to 1.4±1.1 at 6 months follow up (p=0.003).

During the procedure, 15 patients (34.0%) reported some pain but found it to be tolerable and did not require additional anesthesia. Two patients (4.0%) required additional regional anesthesia. Post procedure, 7 patients (15.9%) reported mild pain on the first day. None required oral analgesia beyond the first day of treatment. All patients had mild postoperative inflammation at day 1 in the form of 1+anterior chamber cells with slight conjunctival hyperemia. This inflammation resolved by 2 weeks post treatment in 40 patients (90.9). None of the patients experienced deterioration of their best-corrected visual acuity at final follow-up. One patient who had no light perception before the MicroPulse™ procedure underwent evisceration at 1 month for corneal perforation secondary to infection of a pre-existing bulbous keratopathy. No patient developed hypotony, defined as an IOP of less than 5 mm Hg.

The IOP lowering efficacy of the studied method is comparable to conventional ciliary body photo-coagulation. The rapidity of IOP reduction, seen as early as 1-day post treatment, is an additional advantage over traditional laser treatment. The rapid reduction in IOP seen may be due to enhanced outflow facility from the uveal and suprachoroidal spaces as the novel probe targets the ciliary body epithelium of the pars plicata and/or the pars plana. Delivering treatment in a pulsed mode allows for repetitive series of sub-threshold intensity pulses of energy to be delivered with rest periods in between. "Painting" may also allow for a more even distribution of treatment and effect compared to conventional laser treatment over stationary application sites. A biological response may be triggered to lower IOP and yet excessive thermal damage to the ciliary epithelium and processes is avoided, as seen in histological specimens after conventional laser treatment. The limitation of adjacent tissue damage seen in the MicroPulse™ procedure may also explain the absence of complications such as hypotony.

It is to be understood that the above description is intended to be illustrative and not restrictive. Many embodiments will be apparent to those of skill in the art upon reviewing the above description. The scope of the invention should, therefore, be determined with reference to the appended claims, along with the full scope of equivalents to which such claims are entitled.

The invention claimed is:

1. A contact member for use with a treatment probe for treating a portion of an eye, the contact member comprising:
a main body having a proximal end and a distal end, the proximal end of the main body being coupleable with a distal end of the treatment probe and the distal end of the main body being configured for positioning on a surface of the eye to deliver a treatment beam to the eye;
wherein the distal end of the main body includes a convex contact surface, and wherein the convex contact surface has a 5-50 mm radius of curvature; and
wherein the convex contact surface includes an opening for a treatment fiber that delivers the treatment beam to the eye.

2. The contact member of claim 1, wherein the main body is coupleable with the treatment fiber.

3. The contact member of claim 2, wherein a distal end of the treatment fiber terminates at or protrudes distally from the convex contact surface of the main body.

4. The contact member of claim 2, wherein the distal end of the treatment fiber is centered about the convex contact surface of the main body.

5. The contact member of claim 4, wherein the distal end of the treatment fiber is between 2-5 mm from an edge of the convex contact surface.

6. The contact member of claim 1, wherein the contact member further comprises a registration feature for aligning the treatment probe with a limbus of the eye.

7. The contact member of claim 1, wherein the convex contact surface has a radius of less than 12 mm.

8. The contact member of claim 7, wherein the convex contact surface has a radius between 8-10 mm.

9. The contact member of claim 1, wherein the convex contact surface does not conform to a sclera of the eye.

10. A method for treating a portion of an eye comprising:
providing a treatment probe that includes:
an elongate body having a proximal end and a distal end;
a treatment fiber that is coupled with the elongate body and configured for delivering a treatment beam to the eye; and
a contact member coupled with the distal end of the elongate body, the contact member having a convex contact surface, wherein the convex contact surface has a 5-50 mm radius of curvature and wherein the convex contact surface includes an opening for the treatment fiber;
positioning the convex contact surface of the contact member on a surface of the eye; and delivering the treatment beam to the eye via the treatment fiber.

11. The method of claim 10, wherein a distal end of the treatment fiber terminates at or protrudes distally of the convex contact surface of the contact member.

12. The method of claim 10, further comprising:
maintaining the treatment fiber in sliding contact with a sclera of the eye at a desired distance posterior from a limbus of the eye while sliding the convex contact surface across the surface of the eye; and
delivering the treatment laser.

13. The method of claim 12, further comprising:
sliding the convex contact surface across the surface of the eye along a treatment region that is posterior to a limbus of the eye; and
delivering the treatment beam to the treatment region while sliding the convex contact surface across the surface of the eye.

14. The method of claim 13, further comprising sliding the convex contact surface in an arc motion about the eye.

15. The method of claim 14, wherein the arc motion is less than 180°.

16. The method of claim 14, wherein the arc motion comprises an arc of between 140-160°.

17. The method of claim 14, wherein sliding the convex contact surface comprises sliding between 2-10 traverses in the arc motion in less than 100 seconds.

18. The method of claim 10, wherein delivering the treatment beam comprises delivering a train of beam pulses so as to induce a healing response without coagulation.

* * * * *